US011744473B2

United States Patent
Sheng et al.

(10) Patent No.: US 11,744,473 B2
(45) Date of Patent: Sep. 5, 2023

(54) SELF-LOCKING BLOOD PRESSURE CUFF AND BLOOD PRESSURE MEASURING DEVICE

(71) Applicant: Jiangyu Kangjian Innovation Medical Technology(Chengdu) Co., Ltd, Chengdu (CN)

(72) Inventors: Ying-Wei Sheng, New Taipei (TW); Chieh Kuo, New Taipei (TW); Dai-Hong Cai, Shenzhen (CN); Ying-Chia Tang, New Taipei (TW); Yu-Chao Li, Shenzhen (CN); Lien-Yu Lin, New Taipei (TW); Xue-Pei Xu, Shenzhen (CN)

(73) Assignee: Jiangyu Kangjian Innovation Medical Technology(Chengdu) Co., Ltd, Chengdu (CN)

( * ) Notice: Subject to any disclaimer, the term of this patent is extended or adjusted under 35 U.S.C. 154(b) by 272 days.

(21) Appl. No.: 16/942,998

(22) Filed: Jul. 30, 2020

(65) Prior Publication Data
US 2021/0330204 A1 Oct. 28, 2021

(30) Foreign Application Priority Data
Apr. 26, 2020 (CN) .......................... 202010339128.6

(51) Int. Cl.
*A61B 5/021* (2006.01)
*A61B 17/135* (2006.01)
*A61B 5/022* (2006.01)

(52) U.S. Cl.
CPC .......... *A61B 5/02141* (2013.01); *A61B 5/021* (2013.01); *A61B 5/022* (2013.01); *A61B 5/02233* (2013.01);
(Continued)

(58) Field of Classification Search
CPC ..... A61B 5/021; A61B 5/022; A61B 5/02233; A61B 5/02141; A61B 2560/02; A61B 2560/04; A61B 17/135; A61B 17/132
See application file for complete search history.

(56) References Cited

U.S. PATENT DOCUMENTS 4,353,374 A * 10/1982 Rebbe ................ A61B 5/02233
600/499
5,022,601 A *  6/1991 Saitou .................... B60R 22/405
242/383.1
(Continued)

FOREIGN PATENT DOCUMENTS

CN     106377239 A    2/2017
CN     209122218 U    7/2019

*Primary Examiner* — Nathan J Jenness
*Assistant Examiner* — Thomas Chiang
(74) *Attorney, Agent, or Firm* — ScienBiziP, P.C.

(57) ABSTRACT

A convenient self-locking blood pressure cuff facilitating one-handed use by a user taking his own blood pressure includes a cuff belt, a casing assembly, and a self-locking structure. The self-locking structure is received in the casing assembly. The self-locking structure includes a core shaft, a locking assembly, and a pressing assembly. The core shaft is slidably connected to the casing assembly. The locking assembly and the pressing assembly are wrapped around the core shaft. The locking assembly can rotate when a free end of the cuff belt moves with respect to the casing assembly. The locking assembly can further press against the cuff belt when the core shaft slides in the casing assembly. The pressing assembly presses against the locking assembly to prevent the locking assembly from rotating back.

16 Claims, 5 Drawing Sheets

(52) U.S. Cl.
CPC ......... *A61B 17/135* (2013.01); *A61B 2560/02* (2013.01); *A61B 2560/04* (2013.01)

(56) References Cited

U.S. PATENT DOCUMENTS

| | | | | |
|---|---|---|---|---|
| 6,182,301 | B1* | 2/2001 | Krueger | A47K 13/12 |
| | | | | 4/246.1 |
| 6,575,913 | B1* | 6/2003 | Woolley | F16D 41/12 |
| | | | | 600/490 |
| 11,234,708 | B2* | 2/2022 | Fostad Moe | A61B 17/1327 |
| 2003/0121321 | A1* | 7/2003 | Dempster | E05D 3/12 |
| | | | | 16/223 |
| 2018/0334075 | A1* | 11/2018 | Frank | A61B 17/1327 |
| 2019/0247054 | A1 | 8/2019 | Fostad Moe | |

* cited by examiner

SELF-LOCKING BLOOD PRESSURE CUFF AND BLOOD PRESSURE MEASURING DEVICE

FIELD

The subject matter relates to health monitoring, and more particularly, to a self-locking blood pressure cuff and a blood pressure measuring device.

BACKGROUND

Blood pressure can be measured using a cuff, the cuff is wound around a predetermined location (such as the arm, wrist, or finger) and an airbag is pressurized or inflated to compress an artery at the predetermined location. The cuff may include a fixing mechanism such as a Velcro tape. The Velcro tape includes an outer Velcro on one end of the cuff and an inner Velcro lining on the other end. The outer Velcro and the inner Velcro lining can adhere to each other, thus allowing the cuff to be wound around and fixed at the predetermined location. However, a user measuring his own blood pressure will find one-handed operation of the cuff at least inconvenient if not difficult. Therefore, there is room for improvement in the art.

BRIEF DESCRIPTION OF THE DRAWINGS

Implementations of the present technology will now be described, by way of example only, with reference to the attached figures.

DETAILED DESCRIPTION

It will be appreciated that for simplicity and clarity of illustration, where appropriate, reference numerals have been repeated among the different figures to indicate corresponding or analogous components. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

FIGS. 1 to 4 illustrate an embodiment of a self-locking blood pressure cuff 100, which can be wound around a predetermined part of a human body (for example, an arm or a wrist of a user, not shown), to measure a blood pressure of the user. The cuff 100 includes a cuff belt 10, a casing assembly 20, and a self-locking structure 30. The cuff belt 10 includes a fixed end 101 and a free end 102. The fixed end 101 is fixed to the casing assembly 20. The free end 102 can movably pass through the casing assembly 20, thereby folding the cuff belt 10. Thus, the folded cuff belt 10 can be wound around the predetermined part of the human body. The self-locking structure 30 is disposed in the casing assembly 20, and can lock the cuff belt 10 in place. Thus, the cuff belt 10 can function to allow measurement of blood pressure in the human body.

Figure 4:
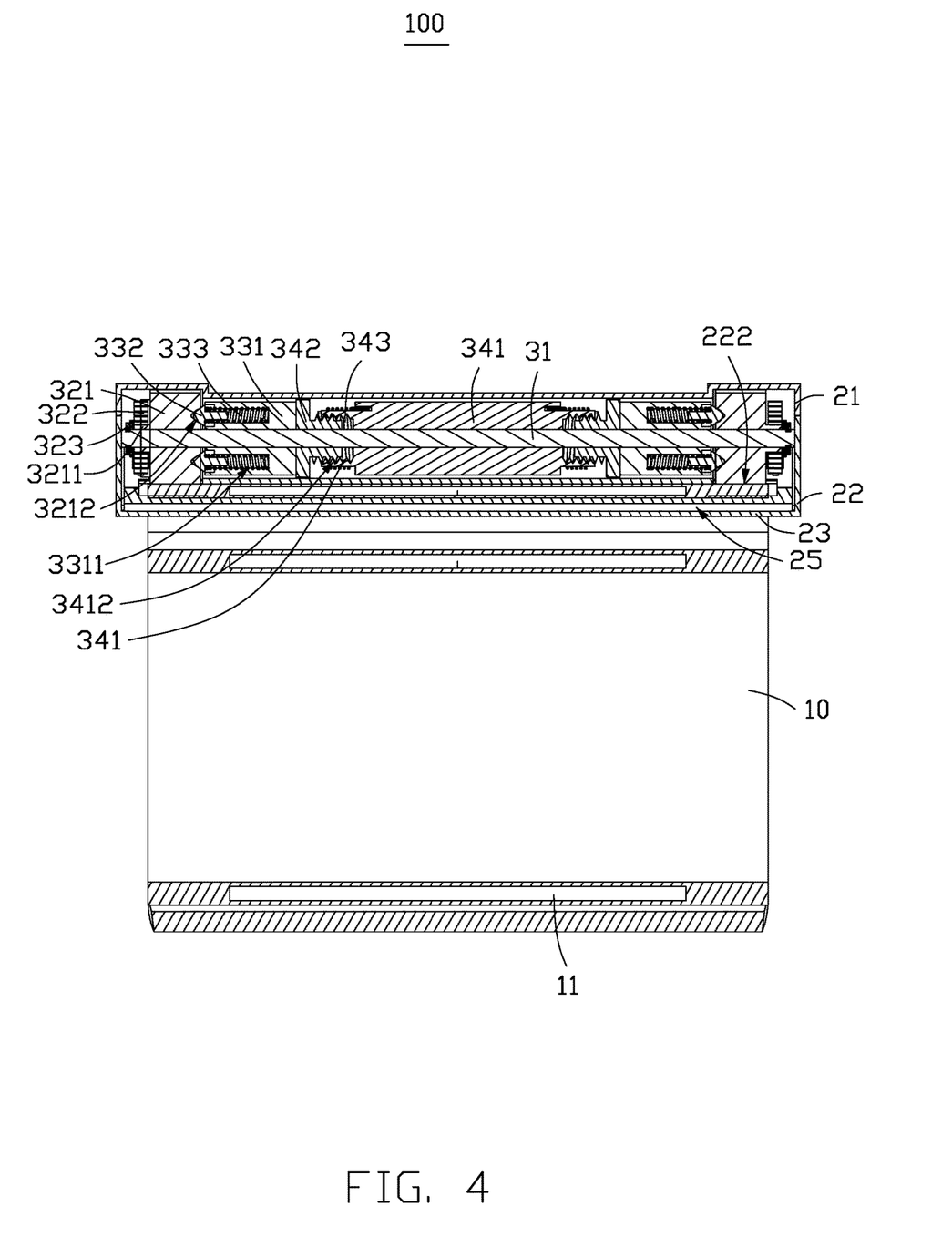
FIG. 4 is a cross-sectional view of the self-locking blood pressure cuff of FIG. 1.

In one embodiment, the cuff belt 10 is fixed to the casing assembly 20 by at least one fastening member (not shown). The fastening member may be a screw. The cuff belt 10 includes an airbag 11, which resists the blood pressure of the user when inflated. The airbag 11 extends along a length direction of the cuff belt 10. FIG. 4 shows a width direction of the airbag 11. The airbag 11 can be detached from the cuff belt 10 to allow cleaning of the airbag 11. The cuff belt 10 can be made of common fabrics.

The casing assembly 20 includes a first casing 21, a second casing 22, and a connecting rod 23. The first casing 21 and the second casing 22 are connected to each other by snap fitting for example, and cooperatively define a receiving cavity 24 for receiving the self-locking structure 30. In one embodiment, the first casing 21 and the second casing 22 when brought together are in shape of a hollow cylinder. In other embodiments, the first casing 21 and the second casing 22 may be integrally formed.

Figure 1:
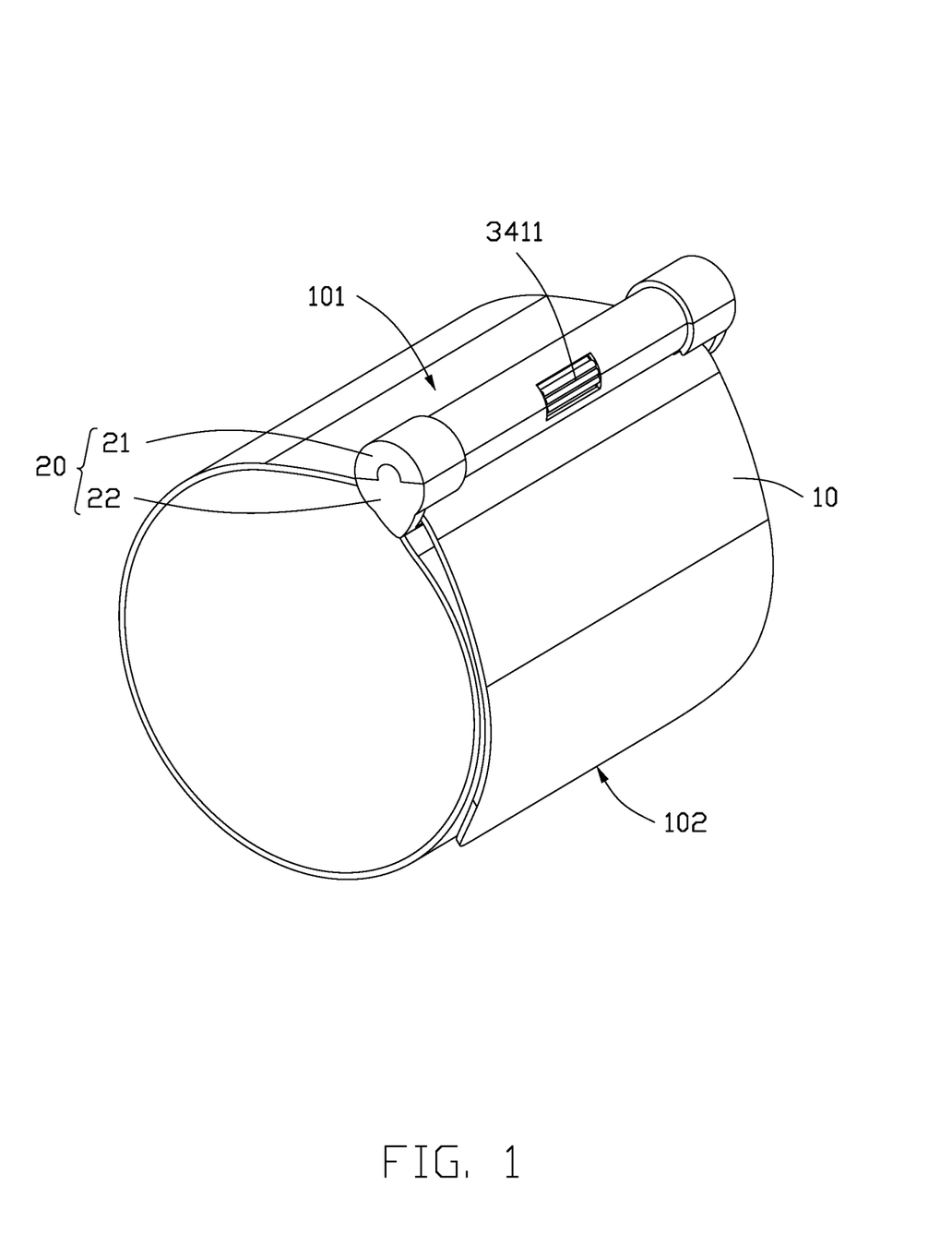
FIG. 1 is a diagrammatic view of an embodiment of a self-locking blood pressure cuff.
Figure 2:
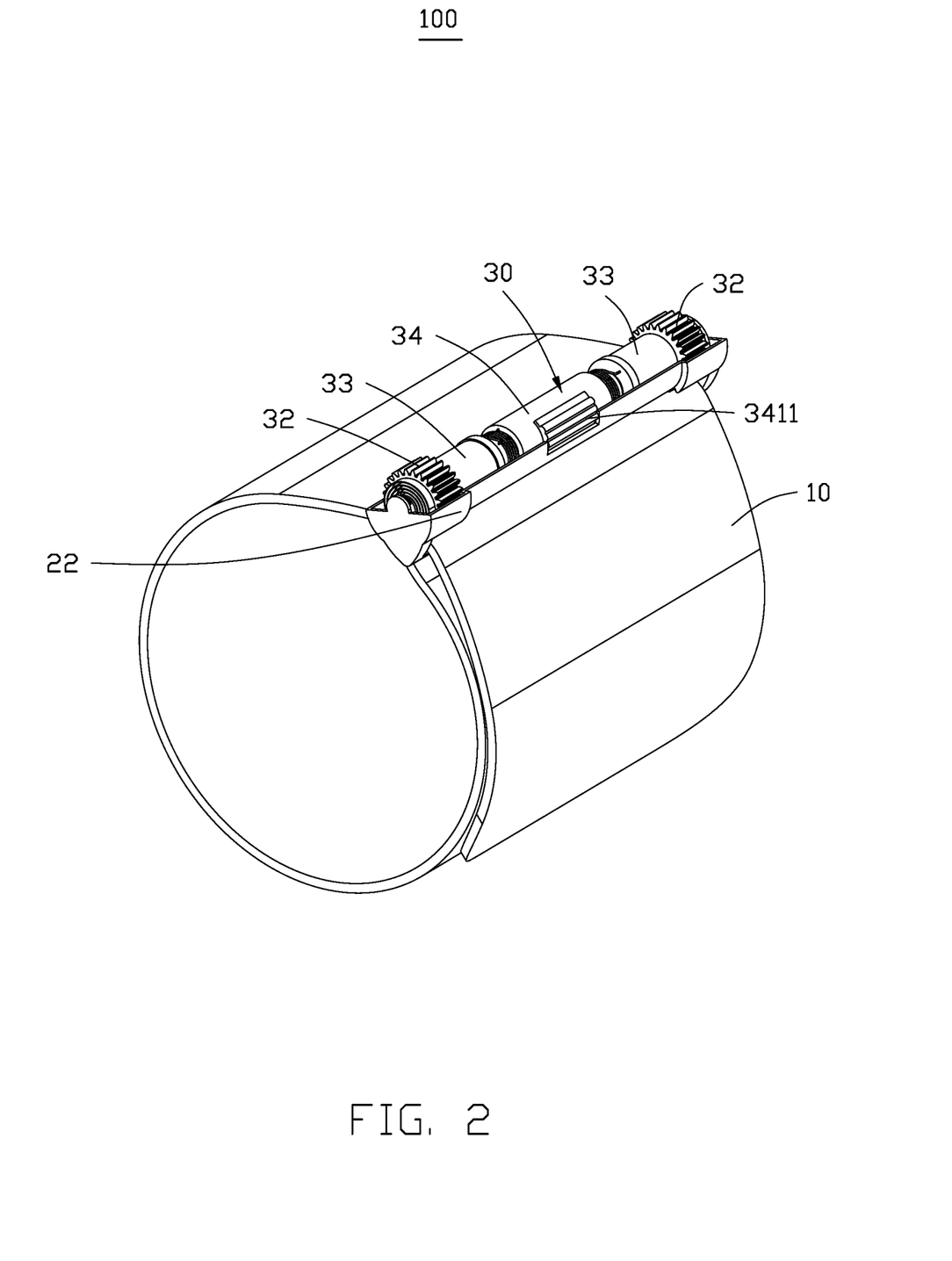
FIG. 2 is a diagrammatic view of the self-locking blood pressure cuff of FIG. 1, when a first casing of the self-locking blood pressure cuff is removed.
Figure 3:
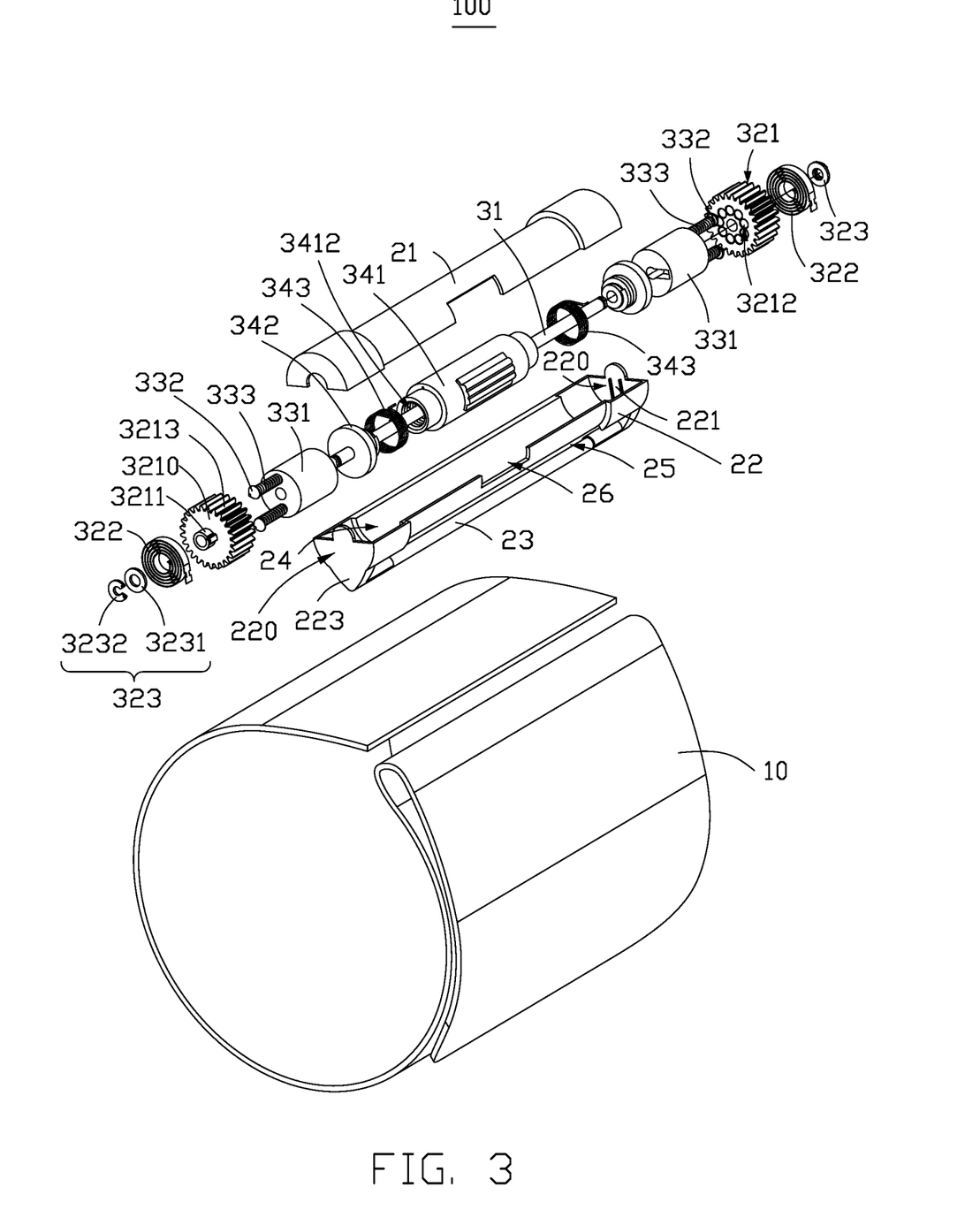
FIG. 3 is an exploded view of the self-locking blood pressure cuff of FIG. 1.

The second casing 22 includes two end walls 220 facing each other. Each end wall 220 defines a sliding groove 221. The sliding groove 221 on one end wall 220 faces the sliding groove 221 on the other end wall 220. The sliding groove 221 extends from the second casing 22 to the first casing 21. The self-locking structure 30 can slide along the sliding groove 221.

The connecting rod 23 is disposed outside the second casing 22 and connected to the second casing 22. The connecting rod 23 and the second casing 22 cooperatively define a channel 25. The free end 102 of the cuff belt 10 can movably pass through the channel 25. The second casing 22 defines at least one first opening 222 facing an end of the connecting rod 23. The first opening 222 is aligned with an end of the sliding groove 221 away from the first casing 21. In one embodiment, the second casing 22 defines two first openings 222. The airbag 11 is disposed between the two first openings 222. In one embodiment, each end wall 220 of the second casing 22 includes a protrusion 223. The protrusion 223 of one end wall 220 faces the protrusion 223 of the other end wall 220. The connecting rod 23 is fixed between the two protrusions 223.

The casing assembly 20 is made of a high-strength material such as plastic or metal. The casing assembly 20 may also be made of a sterilizable material, which improves safety. In other embodiment, the sterilizable material can also be coated on the outer surface of the casing assembly 20.

The self-locking structure 30 includes a core shaft 31, two locking assemblies 32, two pressing assemblies 33, and a loosening assembly 34. Each of the two ends of the core shaft 31 is slidably connected to the sliding groove 221. The two locking assemblies 32, the two pressing assemblies 33, and the loosening assembly 34 are wrapped around the core shaft 31. The two pressing assemblies 33 are disposed at opposite sides of the loosening assembly 34. Each locking assembly 32 is disposed at a side of one pressing assembly 33 facing away from the loosening assembly 34. In one embodiment, the two locking assemblies 32 are disposed at the two ends of the core shaft 31. The loosening assembly 34 is disposed at a middle position of the core shaft 31. In one embodiment, the core shaft 31 is made of a very hard material such as steel or ceramic.

The locking assembly 32 can rotate when the free end 102 of the cuff belt 10 moves inside the channel 25. The locking assembly 32 includes a gear 321, a first torsion spring 322, and a washer 323. The gear 321 is rotatably mounted on the core shaft 31. The first torsion spring 322 is disposed between the gear 321 and the washer 323. The washer 323 is disposed between the sliding groove 221 and the first torsion spring 322. A portion of the gear 321 protrudes from the first opening 222, and presses against the cuff belt 10 passing through the channel 25. In one embodiment, the gear 321 includes a gear body 3210 and a plurality of teeth 3213 disposed on a periphery of the gear body 3210. The teeth 3213 increase friction between the gear 321 and the cuff belt 10, thereby locking the cuff belt 10 in the channel 25. In one embodiment, the teeth 3213 are parallel to an axial direction of the gear body 3210. In other embodiments, the teeth 3213 can be inclined with respect to the axial direction of the gear body 3210.

One end of the first torsion spring 322 is fixed to the gear 321, and the other end of the first torsion spring 322 is fixed to the second casing 22. The first torsion spring 322 is elastically deformed when the gear 321 rotates and, when rebounding, drives the gear 321 to rotate back. In one embodiment, the gear 321 further includes a limiting block 3211 protruding from one side of the gear body 3210 facing the sliding groove 221. The first torsion spring 322 is wrapped around the limiting block 3211. One end of the first torsion spring 322 is fixed to the limiting block 3211. The other side of the gear body 3210 away from the sliding groove 221 defines a plurality of positioning holes 3212. The positioning holes 3212 are disposed around a center of the gear body 3210.

The washer 323 increases area of contact between the first torsion spring 322 and the sliding groove 221. In one embodiment, the washer 323 includes a first washer 3231 and a second washer 3232. The second washer 3232 is disposed between the sliding groove 221 and the first washer 3231.

The pressing assembly 33 presses the locking assembly 32, thereby preventing the locking assembly 32 from rotating back. The pressing assembly 33 includes a first sleeve 331, at least one steel ball 332, and at least one coil spring 333. The first sleeve 331 is wrapped around the core shaft 31. An end of the first sleeve 331 facing the gear 321 defines a plurality of first mounting holes 3311 facing the positioning holes 3212. The coil spring 333 is received and fixed in the first mounting hole 3311. The steel ball 332 is connected to the coil spring 333 and protrudes from the first mounting hole 3311. The steel ball 332 can be inserted into one of the positioning holes 3212, and exert a force preventing the gear 321 from rotating.

The loosening assembly 34 can control a pressure of the pressing assembly 33 applied on the locking assembly 32. The loosening assembly 34 includes a second sleeve 341, two top plates 342, and two second torsion springs 343. The second sleeve 341 is wrapped around the core shaft 31. The second sleeve 341 includes an operating portion 3411. The casing assembly 20 includes a second opening 26. The operating portion 3411 protrudes from the second opening 26, so that the user can rotate the second sleeve 341 through the operating portion 3411. In one embodiment, a portion of the second opening 26 is defined on the first casing 21, and a remaining portion of the second opening 26 is defined on the second casing 22.

Each end of the second sleeve 341 defines a second mounting hole 3412. A screw thread (not labeled) is formed on an inner wall of the second mounting hole 3412. The top plate 342 is rotatably installed in the second mounting hole 3412 through the screw thread. An end of the top plate 342 away from the second sleeve 341 abuts against the first sleeve 331. Each second torsion spring 343 is received in one second mounting hole 3412. One end of the second torsion spring 343 is fixed to the core shaft 31, and the other end of the second torsion spring 343 is fixed to the second sleeve 341. Thereby, the second torsion spring 343 is elastically deformed when the second sleeve 341 rotates, and can rebound when released to drive the gear 321 to rotate back.

Figure 5:
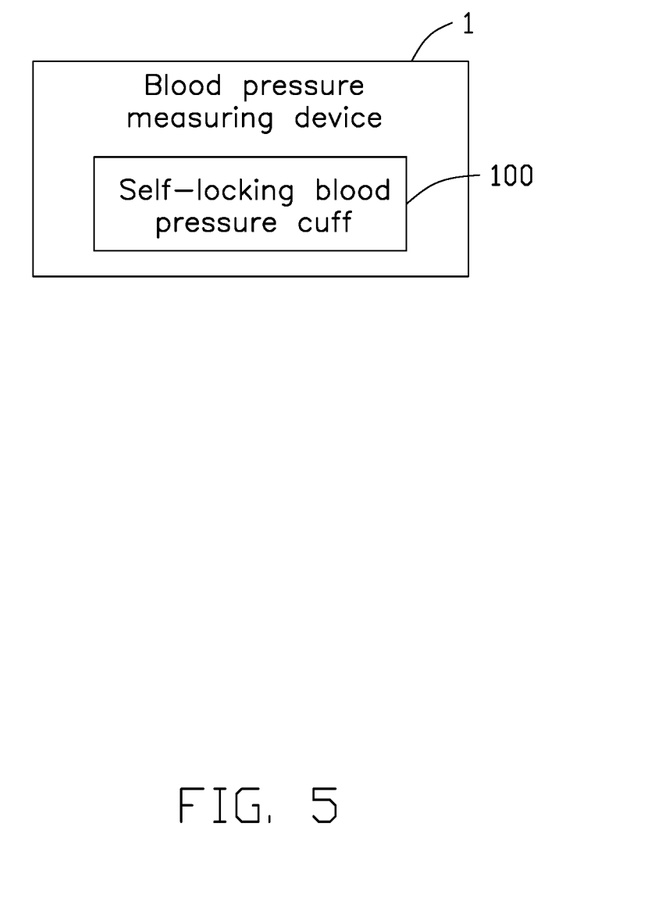
FIG. 5 is a diagrammatic view of an embodiment of a blood pressure measuring device.

FIG. 5 illustrates an embodiment of a blood pressure measuring device 1. The device 1 includes the cuff 100. The device 1 measures the blood pressure of the user through the cuff 100.

To be used, the user can place the free end 102 of the cuff belt 10 in the channel 25 to fold the cuff belt 10. Then, the part of the human body which is the measuring location is placed inside the folded cuff belt 10, and the free end 102 is pulled until the cuff belt 10 is firmly held. Since the portion of the gear 321 protruding from the first opening 222 presses the cuff belt 10, the gear 321 rotates when the cuff belt 10 is pulled in the channel 25, and the first torsion spring 322 is elastically deformed as the gear 321 rotates. The first torsion spring 322 pulls the core shaft 31 to move along the sliding groove 221 toward the connecting rod 23, which decreases a distance between the gear 321 and the cuff belt 10, so that the gear 321 tightly presses the cuff belt 10. Thus, the cuff belt 10 is firmly in place on the human body when the user pulls the second end 102 of the cuff belt 10.

The pressing assembly 33 applies a pressure on the gear 321, thereby preventing the cuff belt 10 from moving back in case the second end 102 is released. The pressure of the pressing assembly 33 applied on the gear 321 is greater than the rebounding force of the first torsion spring 322. Thus, the cuff belt 10 does not move back even if the user knocks or releases the second end 102.

The airbag 11 is inflated to measure the blood pressure of the user. Since the airbag 11 is disposed between the two openings 222, when the gear 321 protruding from the first opening 222 presses the cuff belt 10, the gear 321 does not press against the airbag 11, and accurate measurement of blood pressure is not affected or prejudiced.

After the measurement is completed, the user can rotate the second sleeve 341 to cause the cuff belt 10 to move back. In detail, the second sleeve 341 pushes the top plate 342 to move into the second sleeve 341, which decreases the pressure of the pressing assembly 33 being applied on the gear 321. The coil spring 333 rebounds with the rebounding force of the first torsion spring 322 being greater than the pressure of the pressing assembly 33 applied on the gear 321. Thus, the gear 321 rotates back, thereby driving the cuff belt 10 to move back.

The user can further release the operating part 3411. The second torsion spring 343 rebounds to drive the pressing assembly 33 to again press the gear 321. The second torsion spring 343 and the first torsion spring 322 rebound, and the core shaft 31 moves in the sliding groove 221 away from the connecting rod 23, moving the gear 321 away from the cuff belt 10. Thus, the gear 321 returns to its original state ready for a next measurement of the blood pressure.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A self-locking blood pressure cuff, comprising:
a cuff belt comprising a fixed end and a free end;
a casing assembly, the fixed end fixed to the casing assembly, the free end configured to movably pass through the casing assembly to cause the cuff belt to be folded; and
a self-locking structure received in the casing assembly, the self-locking structure comprising a core shaft, a locking assembly, and a pressing assembly, the core shaft slidably connected to the casing assembly, the locking assembly and the pressing assembly wrapped around the core shaft;
wherein the locking assembly is configured to rotate when the free end of the cuff belt moves with respect to the casing assembly, the locking assembly is further configured to press the cuff belt when the core shaft slides in the casing assembly, the pressing assembly is configured to press the locking assembly to prevent the locking assembly from rotating back; and
wherein the pressing assembly comprises a first sleeve, at least one steel ball, and at least one coil spring, the first sleeve is wrapped around the core shaft, an end of the first sleeve facing a gear defines a plurality of first mounting holes, each of the plurality of first mounting holes faces a respective positioning hole of a gear body of the gear.

2. The self-locking blood pressure cuff of claim 1, wherein the self-locking structure further comprises a loosening assembly wrapped around the core shaft, the loosening assembly abuts against the pressing assembly, and is configured to control a pressure of the pressing assembly applied on the locking assembly.

3. The self-locking blood pressure cuff of claim 2, wherein the casing assembly comprises a first casing and a second casing connected to each other, the second casing comprises two end walls facing each other, each of the two end walls defines a sliding groove, the sliding groove extends along a direction from the second casing to the first casing, and the core shaft is slidably connected to the sliding groove.

4. The self-locking blood pressure cuff of claim 3, wherein the casing assembly further comprises a connecting rod disposed outside and connected to the second casing, the connecting rod and the second casing cooperatively define a channel, and the free end is configured to pass through the channel.

5. The self-locking blood pressure cuff of claim 4, wherein the locking assembly comprises the gear and a first torsion spring, the gear is rotatably mounted on the core shaft, the first torsion spring is disposed between the sliding groove and the gear, a portion of the gear is exposed from the casing assembly and configured to press the cuff belt, one end of the first torsion spring is connected to the gear, and the other end of the first torsion spring is connected to the second casing.

6. The self-locking blood pressure cuff of claim 5, the at least one coil spring is fixedly received in the plurality of first mounting holes, the at least one steel ball is connected to the at least one coil spring and protrudes from the plurality of first mounting holes, the at least one steel ball is configured to insert into the gear to prevent the gear from rotating.

7. The self-locking blood pressure cuff of claim 6, wherein the loosening assembly comprises a second sleeve, a top plate, and a second torsion spring, the second sleeve is wrapped around the core shaft, an end of the second sleeve defines a second mounting hole, the top plate is rotatably installed in the second mounting hole, an end of the top plate away from the second sleeve abuts against the first sleeve, the second torsion spring is received in the second mounting hole, one end of the second torsion spring is fixed to the core shaft, and the other end of the second torsion spring is fixed to the second sleeve.

8. The self-locking blood pressure cuff of claim 7, wherein the second sleeve comprises an operating portion, the casing assembly defines a second opening for exposing the operating portion.

9. A blood pressure measuring device, comprising:
a self-locking blood pressure cuff, comprising:
a cuff belt comprising a fixed end and a free end;
a casing assembly, the fixed end fixed to the casing assembly, the free end configured to movably pass through the casing assembly to cause the cuff belt to be folded; and
a self-locking structure received in the casing assembly, the self-locking structure comprising a core shaft, a locking assembly, and a pressing assembly, the core shaft slidably connected to the casing assembly, the locking assembly and the pressing assembly wrapped around the core shaft;
wherein the locking assembly is configured to rotate when the free end of the cuff belt moves with respect to the casing assembly, the locking assembly is further configured to press the cuff belt when the core shaft slides in the casing assembly, the pressing assembly is configured to press the locking assembly to prevent the locking assembly from rotating back; and
wherein the pressing assembly comprises a first sleeve, at least one steel ball, and at least one coil spring, the first sleeve is wrapped around the core shaft, an end of the first sleeve facing a gear defines a plurality of first mounting holes, each of the plurality of first mounting holes faces a respective positioning hole of a gear body of the gear.

10. The blood pressure measuring device of claim 9, wherein the self-locking structure further comprises a loosening assembly wrapped around the core shaft, the loosening assembly abuts against the pressing assembly, and is configured to control a pressure of the pressing assembly applied on the locking assembly.

11. The blood pressure measuring device of claim 10, wherein the casing assembly comprises a first casing and a second casing connected to each other, the second casing comprises two end walls facing each other, each of the two end walls defines a sliding groove, the sliding groove extends along a direction from the second casing to the first casing, and the core shaft is slidably connected to the sliding groove.

12. The blood pressure measuring device of claim 11, wherein the casing assembly further comprises a connecting rod disposed outside and connected to the second casing, the connecting rod and the second casing cooperatively define a channel, and the free end is configured to pass through the channel.

13. The blood pressure measuring device of claim 12, wherein the locking assembly comprises the gear and a first torsion spring, the gear is rotatably mounted on the core shaft, the first torsion spring is disposed between the sliding groove and the gear, a portion of the gear is exposed from the casing assembly and configured to press the cuff belt, one end of the first torsion spring is connected to the gear, and the other end of the first torsion spring is connected to the second casing.

14. The blood pressure measuring device of claim 13, wherein the at least one coil spring is fixedly received in the plurality of first mounting holes, the at least one steel ball is connected to the at least one coil spring and protrudes from the plurality of first mounting holes, the at least one steel ball is configured to insert into the gear to prevent the gear from rotating.

15. The blood pressure measuring device of claim 14, wherein the loosening assembly comprises a second sleeve, a top plate, and a second torsion spring, the second sleeve is wrapped around the core shaft, an end of the second sleeve defines a second mounting hole, the top plate is rotatably installed in the second mounting hole, an end of the top plate away from the second sleeve abuts against the first sleeve, the second torsion spring is received in the second mounting hole, one end of the second torsion spring is fixed to the core shaft, and the other end of the second torsion spring is fixed to the second sleeve.

16. The blood pressure measuring device of claim 15, wherein the second sleeve comprises an operating portion, the casing assembly defines a second opening for exposing the operating portion.

\* \* \* \* \*